(12) United States Patent
Saito

(10) Patent No.: US 6,270,219 B1
(45) Date of Patent: *Aug. 7, 2001

(54) PLASTIC TRIAL LENS, ITS INJECTION MOLDED ARTICLE AND ITS MOLDING APPARATUS

(75) Inventor: Kiyohiro Saito, Tokyo (JP)

(73) Assignee: Hoya Corporation, Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/117,212
(22) PCT Filed: Dec. 12, 1997
(86) PCT No.: PCT/JP97/04572
 § 371 Date: Jan. 15, 1999
 § 102(e) Date: Jan. 15, 1999
(87) PCT Pub. No.: WO98/26707
 PCT Pub. Date: Jun. 25, 1998

(30) Foreign Application Priority Data

Dec. 17, 1996 (JP) .................................................. 8-336466

(51) Int. Cl.⁷ ................................. G02C 7/06; A61B 3/02
(52) U.S. Cl. ............................................. 351/169; 351/233
(58) Field of Search ..................................... 351/169, 233

(56) References Cited

U.S. PATENT DOCUMENTS

| | | | |
|---|---|---|---|
| 3,981,564 | * 9/1976 | Hoos | 359/826 |
| 4,664,854 | 5/1987 | Bakalar . | |
| 5,596,378 | * 1/1997 | Kelman | 351/233 |

FOREIGN PATENT DOCUMENTS

| | | |
|---|---|---|
| 53-93850 | 8/1978 | (JP) . |
| 60-20201 | 2/1985 | (JP) . |
| 60-150001 | 8/1985 | (JP) . |
| 63-315216 | 12/1988 | (JP) . |
| 2-153709 | 6/1990 | (JP) . |
| 3-193332 | 8/1991 | (JP) . |
| 3-109814 | 11/1991 | (JP) . |
| 4-22902 | 2/1992 | (JP) . |
| 4-294117 | 10/1992 | (JP) . |
| 5-29717 | 4/1993 | (JP) . |
| 7-266391 | 10/1995 | (JP) . |
| 8-220487 | 8/1996 | (JP) . |
| 8-309873 | 11/1996 | (JP) . |
| WO 94/21448 | 9/1994 | (WO) . |

* cited by examiner

Primary Examiner—Scott J. Sugarman
(74) Attorney, Agent, or Firm—Flynn, Thiel, Boutell & Tanis, P.C.

(57) ABSTRACT

A plastic trial lens having a grip portion gripped when the lens is set in trial frames for trial lenses, an injection molded product for making the trial lenses, and a mold assembly for molding the injection molded product are provided. In the injection molded product molded by means of the mold assembly in an injection compression molding machine, a grip portion and a liquid guided and collected area are molded simultaneously with a lens portion on a periphery of the lens portion. When the injection molded product is dipped into hard coat liquid, the hard coat liquid is guided in the liquid guided and collected area to drip down and the remaining liquid without dripping down is collected in the liquid guided and collected area, thereby forming a coating film of uniform thickness on the lens portion. The plastic trial lens which is integrally provided with the grip portion is finished after the liquid guided and collected area is removed.

15 Claims, 14 Drawing Sheets

PLASTIC TRIAL LENS, ITS INJECTION MOLDED ARTICLE AND ITS MOLDING APPARATUS

TECHNICAL FIELD

This invention relates to a plastic trial lens used for testing eyesight and the like of testees, an injection molded product for making the plastic trial lens, and a mold assembly for molding the injection molded product for the plastic trial lens.

BACKGROUND ART

A trial lenses exchanged method, which is a subjective refraction tests, has been adopted for the prescription of glasses for selecting the most suitable lens for each user of glasses for some time. When the trial lenses exchanged method is conducted, a testee wears trial frames for trial lenses. Many kinds of trial lenses with various spherical diopters and astigmatic diopters and the like selected among a set of trial lenses are fitted in trial frames, thereby selecting the most suitable lens for each testee. A trial lens used in the trial lenses exchanged method has a grip portion on a periphery of a lens portion. By gripping the grip portion, the trial lens is set in and taken off from the trial frames.

A conventional trial lens is mainly made of glass. The trial lens is manufactured by attaching a holder ring member with a grip portion on the periphery of the lens cut (edge-filed) into the fixed size (Japanese Utility Model Laid-open No. Hei 4-22902). Some conventional trial lenses are plastic, but the manufacturing process after cutting is the same as that of glass trial lenses.

Besides manufacturing lenses, the conventional trial lens manufacture requires the process of manufacturing members for grip portions with different materials from the lenses and attaching the members on lenses, which takes a lot of time and labor.

Members for grip portions are made of metal in view of durability and easy operation, which causes the disadvantage that a trial lens is heavy as a whole. In complicated prescriptions for glasses for astigmatism, glasses for both far vision and near vision and the like, trial tests are conducted by setting more than one trial lenses one on another in trial frames so that the ears and nose of a testee get a heavy weight, which causes another disadvantage that the trial frames are easy to slip off. The diameter of the trial lens is small so that after-processing such as edge-filing and holder ring attaching is difficult. The grip portion is disposed at the fixed angle, for example, at the upper right or at the upper left of the lens in consideration of setting work in trial frames. In a trial lens with differences between the top and the bottom and between the right and the left, such as a progressive multifocal lens and a lens for an astigmatism, when a holder ring with a grip portion is attached on the periphery of the trial lens, precise positioning of the above fixed angle concerning the grip portion is required in accordance with an optical layout in the design of the lens about an optical center position and the like, which makes the attaching process of the holder ring difficult in a trial lens with a short diameter. Moreover, when the holder ring with the grip portion is caulked too strongly on the periphery of the lens, in a plastic lens, this situation causes an optical surface to be deformed, which brings about optical distortion and the like.

An object of the present invention is to provide a plastic trial lens, in which the process of manufacturing a member for a grip portion with different materials from a lens and attaching the member on the lens is omitted, the whole trial lens is more light-weight and the precise layout of the grip portion in relation to the lens portion is obtained, and an injection molded product to make the plastic trial lens, and moreover, a mold assembly to mold the injection molded product.

DISCLOSURE OF THE INVENTION

A plastic trial lens according to the present invention is provided with a lens portion and a grip portion integrally formed on a periphery of the lens being gripped when the lens portion is set in trial frames for trial lenses, the grip portion being molded simultaneously with the lens portion.

The trial lens according to the present invention is plastic, in which the grip portion is integrally molded with the lens portion. The lens portion and the grip portion are molded out of the same synthetic resin, the grip portion being molded simultaneously with the lens portion, which omits the process of attaching a member for the grip portion on the lens portion. The grip portion is formed out of the same synthetic resin as the lens portion so that the whole trial lens is lightweight. The grip portion is integrally molded with the lens portion after being positioned in a mold assembly so as to be formed in the fixed position of the lens portion, and hence the grip portion is disposed in relation to the lens portion in a fixed position accurately laid out.

An injection molding method, an injection compression molding method or a casting method (cast molding method) can be adopted to manufacture the above-described plastic trial lens in which the lens portion and the grip portion are integrally molded.

However, the casting method uses thermosetting resins (diethylene glycol bisuallyl carbonate is typical) for materials. The polymerization shrinkage percent of thermosetting resin is as large as about 14 percent. Therefore, the difference between a lens shape in design and a real mold transfer shape is large so that extremely high manufacturing technology is required to make precision mold transfer of a molded product attain the high precision required for the trial lens. In addition, molding a plastic lens by means of the casting method requires a molding time from 12 to 24 hours to precisely control the polymerization of the resin for the materials. As a result, one cycle of molding time becomes long, thus making mass-production of trial lenses costly. For the reasons stated above, it is preferable that the plastic trial lens is molded by means of the injection molding method or the injection compression molding method in which any disadvantage as described above does not occur.

When the plastic trial lens is molded by means of the injection molding method or the injection compression molding method, the thermoplastic resin used for the materials is such as a PMMA (polymethyl methacrylate) system resin or a PC (polycarbonate) system resin.

A holder ring can be attached on the periphery of the lens portion of the plastic trial lens, but it is preferable that an edge portion instead of the holder ring is integrally provided on the periphery of the lens portion, the edge portion being molded simultaneously with the lens portion.

Using the edge portion instead of the holder portion helps the trial lens to be more lightweight and omits a member for the holder ring. In addition, the process requiring the holder ring to be caulked on the periphery of the lens portion is unnecessary, which secures a high optical precision of the lens portion.

The plastic trial lens according to the present invention can be a progressive multifocal lens with a portion for far vision, a portion for near vision and a progressive portion between the portion for far vision and the portion for near vision or a lens for an astigmatism. The present invention is applicable to both a single vision lens and a multifocal lens which has a portion for near vision and a portion for far vision but no progressive portion.

When the trial lens is a progressive multifocal lens, it is preferable that the lens is provided with a mark indicating the direction of a horizontal datum line and a grip portion shifting to the right or the left from the center between the right portion and the left portion of the lens portion on the periphery of the lens portion according to the lens for a right eye or for a left eye.

Thus, the distinction between a lens for a right eye and a left eye in each progressive multifocal trial lens and the horizontal direction are clearly known with the position of the grip portion and the mark. As a result, while distinguishing the trial lens for a right eye from that for a left eye, the position of revolving direction of the round shaped lens portion as a whole in each trial lens is accurately fixed so that the trial lens can be fitted in the trial frames in an accurate position.

Also, a diopter measuring position in the portions for far vision and for near vision in the lens portion or a layout of optical center can be easily known with the grip portion and the mark.

The mark for indicating a horizontal datum line can be provided after the lens is molded by means of injection molding and also molded simultaneously with the lens portion and the grip portion. If the mark is molded simultaneously as described above, a manufacturing process is cut, thus improving the manufacturing efficiency.

When the mark is molded simultaneously with the lens portion and the grip portion, the mark is formed as an indented portion or a projected portion in the lens portion. However, it is preferable that the mark is not a projected portion but an indented portion. If the mark is a projected portion, the projected portion becomes a hindrance, for example, it catches in the trial frames when the trial lens is fitted in the trial frames. The indented portion as the mark can be indented from one surface of the lens portion and also cut deep in an inside diametrical direction of the lens portion. Moreover, it is possible to combine the above two ways.

Many sorts of diopters are provided in the aforesaid progressive multifocal lens. The present invention is applicable to trial lenses with various diopters, to take an example, a lens with 0.00 diopter in a portion for far vision in which the diopter for near vision is fixed only in a portion for near vision. This type of trial lens can be set in the trial frames with a single vision trial lens for far vision or near vision one on another.

An injection molded product for making the plastic trial lens according to the present invention is provided with a lens portion, a liquid guiding and collecting area integrally formed on a periphery of the lens portion in which coating liquid flowing down on the surfaces of the lens portion is guided and collected when the lens is dipped into and pulled up from the coating liquid, and a grip portion gripped when the lens portion is set in the trial frames after the liquid guiding and collecting area is removed. The liquid guiding and collecting area and the grip portion are molded simultaneously with the lens portion.

The dipping process requiring that the injection molded product be dipped into the coating liquid is conducted to form a coating film made out of the hard coating liquid on surfaces of the trial lens. The hard coating film improves the abrasion-resistance and durability of the trial lens.

When the injection molded product with the lens portion is dipped into and pulled up from the coating liquid, the coating liquid flows down on the surfaces of the lens portion, while a coating liquid collecting portion is formed at the bottom of the lens portion. This causes a difference in the thickness of a coating film between a part nearby and a part far from the liquid collecting portion, thus changing the curvature of a lens surface, which sometimes affects the lens diopter. As a result, serious disadvantages may occur from the viewpoint of the precision of the trial lenses.

In the present invention, when the lens portion is molded by means of the injection molding method or the injection compression molding method, the liquid guiding and collecting area, as well as the grip portion, is molded at the same time on the periphery of the lens portion. The liquid guiding and collecting area is formed to guide the coating liquid flowing down on the surfaces of the lens portion when the injection molded product is dipped into and pulled up from the coating liquid, and to collect the remaining liquid without dripping. Consequently, a liquid collecting portion is formed in the liquid guiding and collecting area so as to ease the effects on the lens portion by the liquid collecting portion, which virtually assures the uniformity in thickness of the coating film.

When the liquid guiding and collecting area having the above-described effects is formed in the injection molded product for the trial lens, in the present invention, the liquid guiding and collecting area as well as the grip portion is simultaneously molded on the periphery of the lens portion, thereby facilitating the molded process.

The shape of the liquid guiding and collecting area is optional if the coating liquid flowing down on the surfaces of the lens portion can be guided and the remaining liquid without dripping down can be collected in the area when the injection molded product is dipped in and pulled up from the coating liquid, for example, a bar shape extending in an outside diametrical direction of the lens portion (downward when pulled up from the coating liquid) or a fan shape with a small projection in an outside diametrical direction and two long sides extending in a circumferential direction is available.

The liquid guiding and collecting area is, however, removed when the lens portion is set in the trial frames by gripping the grip portion after the trial lens is finished. In order to facilitate the removing process and keep the liquid collecting portion formed of the coating liquid flowing down on the surfaces of the lens portion away from the lens portion, the liquid guiding and collecting area is preferably shaped into a bar extending in an outside diametrical direction.

The grip portion and the liquid guiding and collecting area integrally molded on the periphery of the lens portion can be formed in an optional positional relationship, but preferably the grip portion and the liquid guiding and collecting area are formed opposite to each other on the periphery of the lens portion.

As a result, when the injection molded product is dipped into the coating liquid, by placing the liquid collecting and guiding area downward and the grip portion upward, the injection molded product is dipped into the coating liquid by supporting the grip portion with a supporting utensil such as a clip. Moreover, when the injection molded product is pulled up from the coating liquid, the coating liquid collecting portion is formed in the liquid guiding and collecting area that is disposed downward, thereby forming a coating film of a uniform thickness on the surfaces of the lens portion as predetermined.

In the above case, the grip portion is used to be gripped when the lens portion is set in the trial frames and also used as a portion to be supported with the supporting utensil when the injection molded product with the lens portion is dipped into the coating liquid.

In the injection molded product, one lens portion can be formed or more than one lens portion can be formed in two-dimensional or three-dimensional positional relationship, that is, the injection molded product can make one lens or more than one lens.

In the injection molded product for making more than one lens, preferably more than one lens portion are coupled to each other by means of a coupling portion, the coupling portion being provided with a portion supported when the lens portions are dipped into the coating liquid, and the liquid guiding and collecting area is formed on an opposite side to the supported portion on a periphery of each lens portion.

Consequently, each lens portion is dipped into the coating liquid by supporting the supported portion disposed upwardly with the supporting utensil. Thus, all lens portions are dipped into the coating liquid at the same time and the liquid collecting portion is formed in each liquid guiding and collecting area, since each liquid guiding and collecting area is disposed downward when each lens portion is pulled up from the coating liquid.

In the above-described injection molded product for making the trial lens, the grip portion and the liquid guiding and collecting area are separately formed. However, an injection molded product with a portion serving both as a grip portion and a liquid guiding and collecting area can be manufactured.

In other words, this type of injection molded product for the trial lens is provided with a lens portion and a grip portion molded simultaneously with the lens portion on the periphery of the lens portion being gripped when the lens portion is set in trial frames. Since the grip portion is disposed downward when the lens portion is dipped into the coating liquid, the grip portion also serves as a liquid guiding and collecting area in which the coating liquid flowing down on surfaces of the lens portion is guided and collected when the lens portion is pulled up from the coating liquid.

The injection molded product for the trial lens can be an injection molded product for a progressive multifocal lens with a portion for far vision, a portion for near vision and a progressive portion between the portion for far vision and the portion for near vision or an injection molded product for a lens for an astigmatism. In addition, the injection molded product is applicable to both a single vision lens and a multifocal lens which has a portion for far vision and a portion for near vision but no progressive portion.

When a progressive multifocal lens is obtained from the injection molded product, as described above, the progressive multifocal lens has 0.00 diopter in a portion for far vision in which the diopter for near vision is fixed only in a portion for near vision. This type of trial lens can be set in the trial frames with a single vision trial lens for far vision or near vision one on another.

When the lens portion in the injection molded product is a progressive multifocal lens portion with a portion for far vision, a portion for near vision and a progressive portion between the portion for far vision and the portion for near vision, the grip portion is preferably formed on the periphery of the side of the portion for far vision out of both sides of portions for far vision and near vision in the lens portion. When the grip portion is formed on the periphery of the side of the portion for near vision in the lens portion, a groove depending on the sectional shape of the portion for near vision is formed in a boundary between an edge portion and the portion for near vision in the lens portion so that the coating liquid is likely to be collected in the groove. When the grip portion is formed on the periphery of the side of the portion for far vision in the lens portion, the above-mentioned disadvantage does not occur, thus securing high optical precision of the lens portion.

The injection molded product for the trial lens, in which the grip portion serves as the liquid guiding and collecting area, is provided with a supported portion supported with a supporting utensil when the injection molded product is dipped into the coating liquid. The supported portion can be formed in an optical positional relationship to the grip portion, but preferably the supported portion is formed on the opposite side to the grip portion on the periphery of the lens portion.

As a result, when the injection molded product is dipped into the coating liquid, by placing the grip portion downward and the supported portion upward, the injection molded product is dipped into the coating liquid by supporting the supported portion with a supporting utensil such as a clip. Moreover, when the injection molded product is pulled up from the coating liquid, the coating liquid collecting portion is formed in the grip portion that is disposed downward, thereby forming a coating film of uniform thickness on the surfaces of the lens portion as predetermined.

Preferably, the supported portion is molded simultaneously with the lens portion and the grip portion, which can shorten the manufacturing process.

The shape of the supported portion is optional if it can be surely supported with the supporting utensil, for example, a bar shape extending in an outside diametrical direction of the lens portion or a fan shape with a small projection in an outside diametrical direction and two long sides extending in a circumferential direction is available.

The supported portion is, however, removed when the lens portion is set in the trial frames by gripping the grip portion after the trial lens is finished. In order to facilitate the removing process, the supported portion is preferably shaped into a bar extending in an outside diametrical direction of the lens portion and having a small connecting area with the lens portion.

A mold assembly for molding the injection molded product for the plastic trial lens according to the present invention is provided with two molds to be parted, a pair of inserts disposed in each of the molds which form a cavity for molding the plastic trial lens by a molten synthetic resin filled therein when the molds are mold-closed. The cavity includes a lens molded portion to mold the lens portion of the trial lens and a grip molded portion to mold the grip portion on the periphery of the lens portion being gripped when the lens portion is set in trial frames.

In the mold assembly, the cavity between a pair of the inserts includes the lens molded portion and the grip molded portion. Therefore, when the molten synthetic resin is filled in the cavity, the lens portion and the grip portion of the trial lens are molded at the same time.

The molds to be parted in the mold assembly consist of a top mold and a bottom mold or a right mold and a left mold. In other words, the mold assembly can be structured both vertically and horizontally.

The injection molded product for the trial lens molded in the mold assembly can be the injection molded product for a progressive multifocal lens with a portion for far vision, a portion for near vision and a progressive portion between the portion for far vision and the portion for near vision or the injection molded product for a lens for astigmatism. In addition, the injection molded product is applicable to both a single vision lens and a multifocal lens which has a portion for far vision and a portion for near vision but no progressive portion.

The mold assembly can be used for molding more than one progressive multifocal trial lenses with different additions. In this case, it is preferable that the mold assembly is provided with more than one set of a pair of inserts, the lens portion molded between more than one set of the inserts is a progressive multifocal lens portion with a portion for far vision, a portion for near vision and a progressive portion between the portions for far vision and for near vision, a spacer for adjusting the thickness of the lens is disposed on the back side of one insert out of a pair of the inserts opposite to each other, and more than one spacer having different thicknesses are provided in more than one set of the inserts so that more than one progressive multifocal lens with different additions are molded by means of the spacers having different thicknesses.

A concave surface side of the progressive multifocal lens portion that is a meniscus lens is a spherical surface with a fixed curvature. By the curvature of a convex surface side which is an aspheric surface, the shape of the lens surface and the diopter change. As the addition is enlarged, the thickness of the center of the lens becomes large and the volume of the lens increases. When more than one lens portion with different additions are molded in the mold assembly at the same time, a large difference in volume among the lens portions affects the molding conditions, which makes it difficult to secure high optical precision for all the lens portions. In the present invention, to virtually fix the volume of each lens portion regardless of the addition, first an intermediate addition is set, then the lens thickness of the lens portion with the intermediate addition is found and this thickness becomes a standard against which the thickness of each of the other lens portions with different additions is redesigned. In a lens portion with an addition smaller than the above intermediate value, the volume of the lens is increased, while in a lens portion with an addition larger than the above intermediate value, the volume of the lens is decreased.

With regard to the spacer, spacers with thicknesses larger than and smaller than the spacer with the intermediate thickness are made so as to obtain less portions with additions larger than and smaller than the intermediate addition. The spacers having different thicknesses are disposed on the back of the insert on one side out of more than one set of the inserts so that a difference in capacity (volume of the lens portion) among more than one cavity to mold more than one sort of progressive multifocal lens portion with different additions is adjusted. As a result, molding conditions in each trial lens portion formed by filling the molten synthetic resin in the cavity become almost uniform, which raises the mold transfer efficiency in each cavity and ensures high optical precision.

In the mold assembly according to the present invention, a back insert can be disposed on the back side of one of a pair of the inserts and the position of a molded surface of the lens portion in one insert in relation to the other insert can be established by the length of the back insert.

The position of the molded surface of the lens portion in one insert in relation to the other insert is established by the length of the back insert. Therefore, only the molded surface of the lens portion is required to have high-precision finishing in one insert, which can facilitate the work of manufacturing and processing the above one insert.

The cavity formed between a pair of the inserts can include an edge molded portion to mold the edge portion serving as the holder ring on the periphery of the lens portion.

In this case, in the plastic trial lens obtained from the injection molded product, the holder ring does not need to be attached on the periphery of the lens portion, thus simplifying the manufacturing process of the trial lens.

A grip molded portion to mold the grip portion on the periphery of the lens portion can be formed in relation to a lens molded portion to mold the lens portion in an optional circumferential directional position. However, preferably, the grip molded portion is formed between a gate from which molten synthetic resin flows into the cavity and the lens molded portion in the cavity.

When the molten synthetic resin flows into the cavity from the gate, the molten synthetic resin is filled in the lens molded portion through the grip molded portion so that distortion by filling the molten synthetic resin is easy to break out in a portion of resin near the gate, but the distortion occurs in the portion of resin filled in the grip molded portion, which prevents distortion from breaking out in a portion of resin filled in the lens molded portion, thus securing a high precision of the lens.

A pair of the inserts to form the cavity can be formed with each member disposed in each mold to be parted, but preferably a pair of the inserts respectively include an inner insert member to mold the lens portion and an outer insert member disposed on the outside of the inner insert member to mold the grip portion.

Consequently, when more than one kind of trial lenses with different additions in the lens portions, which are provided with the grip portions integrally on the periphery of the lens portions, are manufactured, only the inner inserts are exchanged and the outer insert can be used in common for more than one kind of the trial lens.

Materials for members composing the mold assembly can be metal, ceramic or glass, and in addition, the above different kinds of materials can be used for more than one member.

BEST MODE FOR CARRYING OUT THE INVENTION

Figure 1:
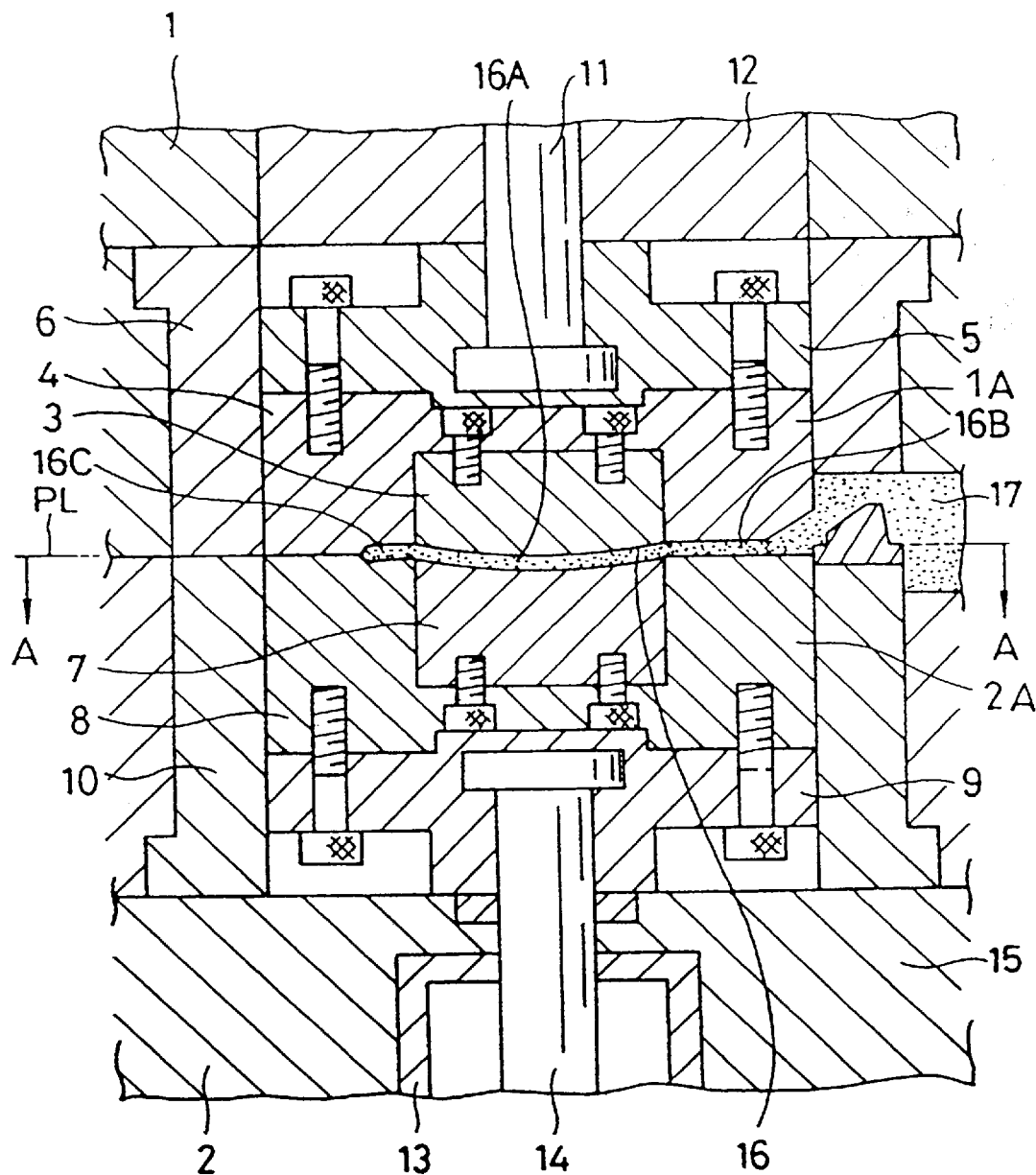
FIG. 1 is a schematic sectional view of the principal portion of a mold assembly of an injection molding machine.

The present invention is explained more in detail in accordance with the accompanying drawings. A mold assembly in an injection molding machine to mold an injection molded product for making a plastic trial lens includes a top mold 1 and a bottom mold 2, both of which a parting line PL divides as illustrated in FIG. 1. The top mold 1 contains an outer insert member 4 in the center of which an inner insert member 3 is fixed and an insert base 5 having mounted thereunder the outer insert member 4, all of which are slidably guided inside an upper insert guide 6. The bottom mold 2 contains an outer insert member 8 in the center of which an inner insert member 7 is fixed, and an insert base 9 having mounted thereon the outer insert member 8, all of which are slidably guided inside a lower insert guide 10.

The insert base 5 in the top mold 1 is coupled with a piston rod 11 which extends in a downward direction from an upper cylinder (not shown). When the piston rod 11 retracts (goes up), the insert base 5 abuts on a back insert 12. The insert base 9 in the bottom mold 2 is coupled with a piston rod 14 which extends in an upward direction from a lower cylinder 13. When the piston rod 14 retracts (goes down), the insert base 9 abuts on a mold plate 15. In this position, the outer insert 8 and the like become fixed.

The inner and outer insert members 3 and 4 in the top mold 1 form an insert 1A and the inner and outer insert members 7 and 8 in the bottom mold 2 form an insert 2A. When the top mold 1 and the bottom mold 2 are mold-closed, between a pair of the insert 1A and the insert 2A disposed vertically a cavity 16 for molding the injection molded product for the trial lens is formed.

Figure 2:
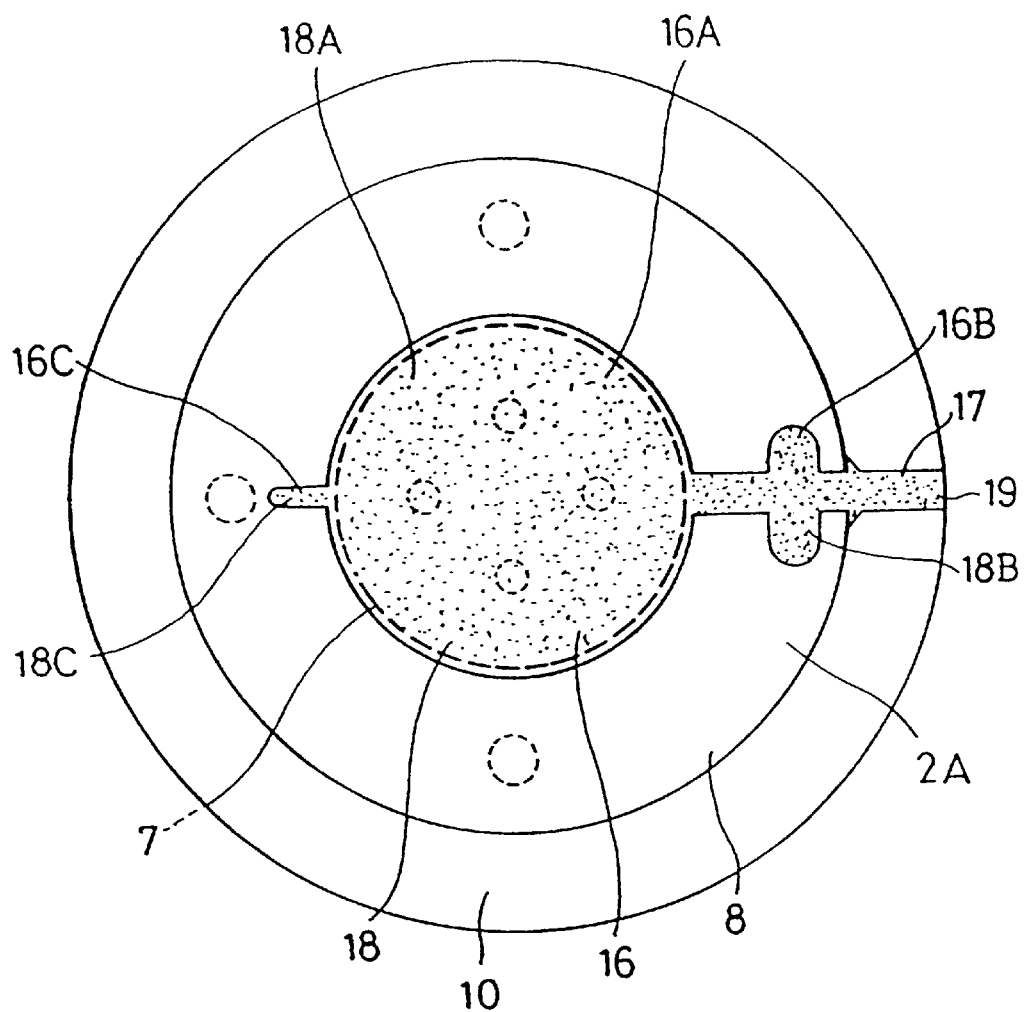
FIG. 2 is a schematic plane view taken along the A-A line in FIG. 1.

As illustrated in FIG. 2, the cavity 16 is composed of a lens molded portion 16A, a grip molded portion 16B, and a liquid guiding and collecting area molded portion 16C. The grip molded portion 16B is provided with a runner 17, the runner 17 being linked to a sprue, the sprue being connected to an injection nozzle of the injection molding machine.

As shown in FIG. 1, the inner insert member 3 in the top mold 1 and the inner insert 7 in the bottom mold 2, both of which are vertically disposed opposite to each other, form the lens molded portion 16A. Also, the outer insert member 4 in the top mold 1 and the outer insert 8 in the bottom mold 2, both of which are vertically disposed opposite to each other, form the grip molded portion 16B and the liquid guiding and collecting area molded portion 16C.

When the top mold 1 and the bottom mold 2 are mold-closed with a clamping cylinder, heated molten synthetic resin is injected from the injection nozzle into the sprue and the molten synthetic resin is filled in the sprue, the runner 17 and the cavity 16, and then gradually cools and solidifies.

Subsequently the top mold 1 and the bottom mold 2 are mold-opened from the parting line PL, and upon operation of ejecting means (not shown) a primary injection molded product 18 in FIG. 2 is taken out. In the same positional relationship with the lens molded portion 16A, the grip molded portion 16B, and the liquid guiding and collecting area molded portion 16C, the primary injection molded product 18 is integrally formed with a grip portion 18B and a liquid guiding and collecting area 18C in an opposite position to each other on a periphery of a lens portion 18A. The grip portion 18B is linked to a portion 19 formed in the runner 17, the portion 19 being linked to a portion formed in the sprue. The grip portion 18B, the liquid guiding and collecting area 18C and the like are molded simultaneously with the lens portion 18A.

Figure 3:
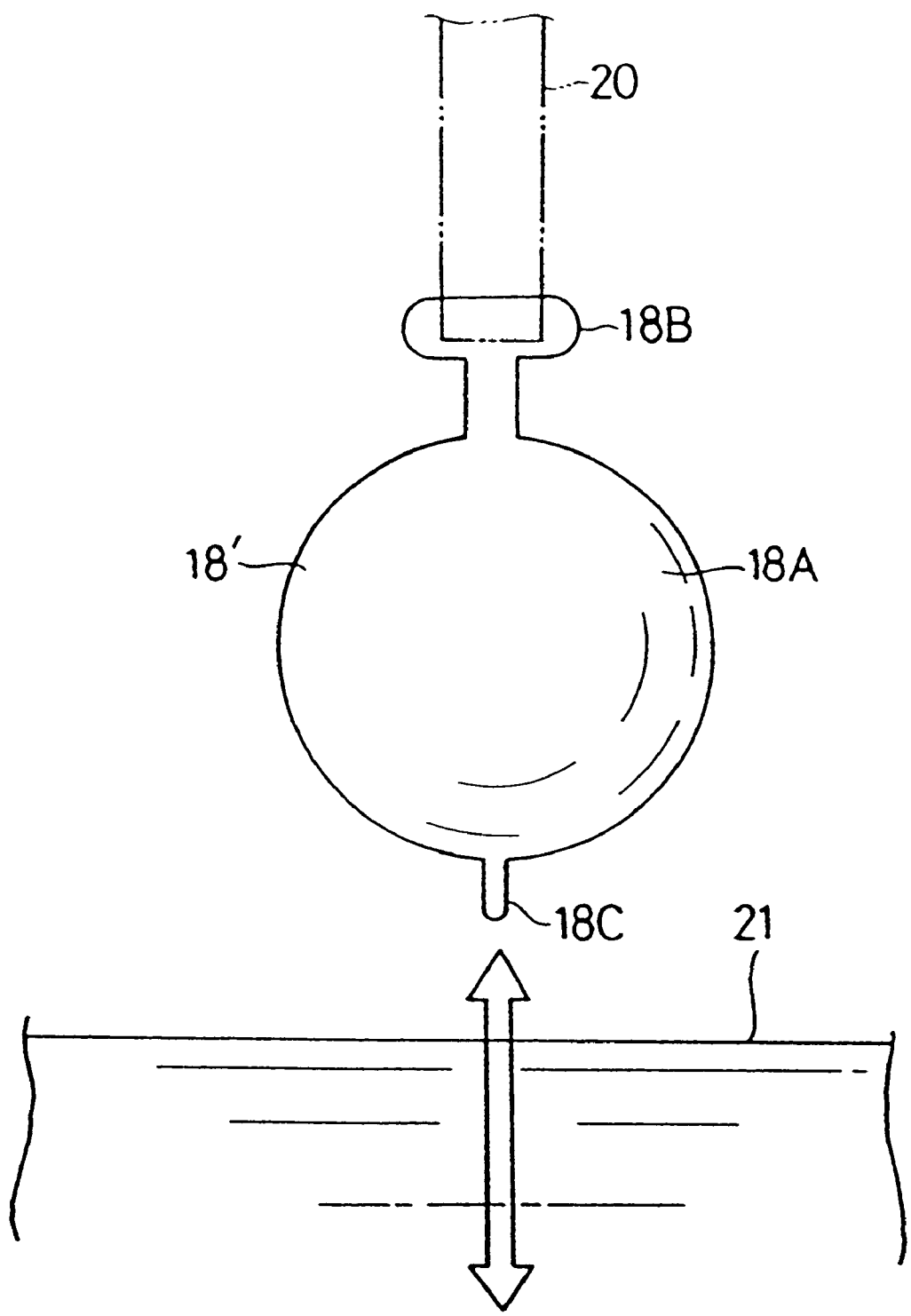
FIG. 3 is an explanatory view showing the process of coating an injection molded product provided with a liquid guiding and collecting area molded by means of the mold assembly in FIG. 1 and FIG. 2.

The primary injection molded product 18 manufactured as described above is cut between the grip portion 18B and the portion 19, thereby making a secondary injection molded product 18' shown in FIG. 3 which is composed of the lens portion 18A, the grip portion 18B, and the liquid guiding and collecting area 18C. After completion of predetermined treatments such as washing, the secondary injection molded product 18' is treated by dipping, that is, the secondary injection molded product 18' is dipped into a hard coating liquid 21 that is, for example, a silicon or acrylic coating liquid. Coating is conducted by placing the grip portion 18B upward and the liquid guiding and collecting area 18C downward, then supporting the grip portion 18B that is disposed upward with a supporting utensil 20 such as a clip.

The secondary injection molded product 18' is pulled up, after being dipped into the hard coating liquid 21 at least above the boundary part between the lens portion 18A and the grip portion 18B. At this time, a surplus of hard coating liquid covering surfaces of the lens portion 18A flows down on the lens surfaces and is guided to the liquid guiding and collecting area 18C for dripping down.

Furthermore, a small amount of the remaining liquid without dripping down forms a liquid collected portion in the liquid guiding and collecting area 18C, but not in the lens portion 18A.

Figure 4:
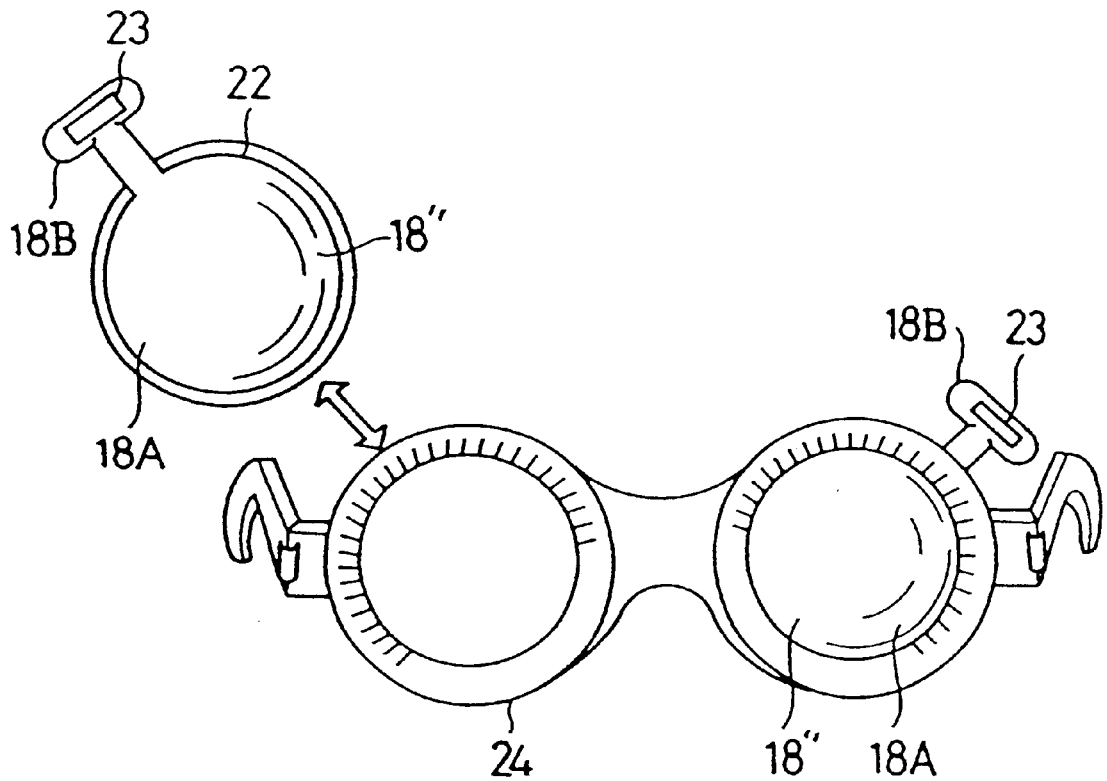
FIG. 4 is an explanatory view showing the process of setting a plastic trial lens in trial frames for trial lenses, the plastic trial lens being manufactured by removing the liquid guiding and collecting area from the injection molded product in FIG. 3.

Next, by UV-hardening (hardening by ultraviolet irradiation) and heat-drying the secondary injection molded product 18', the surfaces of the lens portion 18A are covered with a coating film made from a hard coating liquid. As illustrated in FIG. 4, the liquid guiding and collecting area 18C is removed from the lens portion 18A by cutting and the like. A holder ring 22 is attached on the periphery of the lens portion 18A and, moreover, a label 23 indicating the diopter of the trial lens and other information is stuck to the grip portion 18B, thereby finishing a plastic trial lens 18".

An edge portion made of a thick portion and the like, instead of the holder ring, can be molded on the periphery of the lens portion 18A simultaneously with the lens portion 18A, the grip portion 18B and the liquid guiding and collecting area 18C. Even when a holder ring is attached on the periphery of the lens portion 18A by caulking without forming the edge portion on the periphery of the lens portion 18A, the holder ring 22 does not need to be strongly caulked, since the grip portion 18B is integrally molded in the predefined laid-out position of the lens portion 18A.

Instead of using the label 23, the indication of lens diopter and other information on the grip portion 18B can be made with a mark engraved on a mold component member at the time of molding by means of the mold assembly in the injection molding machine As shown in FIG. 4, the trial lens 18" is exchangeably set in trial frames for trial lenses 24 for testing eyesight and the like of testees. The trial lens 18" is set in the trial frames 24 and removed therefrom by gripping the grip portion 18B.

A trial lens according to the above-described embodiment is a progressive multifocal lens with 0.00 diopter in a portion for far vision and an outside diameter of 35 millimeter. The primary injection molded product 18 can be molded for making more than one lens with more than one progressive multifocal lens portion 18A. In this case, more than one lens portion 18A needs to be a progressive multifocal lens portion. Additions of the progressive multifocal lens portion 18A are five kinds ranging from 1.00 diopter to 3.00 diopter at an interval of 0.5 pitch as required, and two lens portions 18A with the same addition can be molded at every shot by the injection molded machine. Consequently, a total of ten lens portions 18A with the whole range of diopters having the necessary five kinds of additions can be molded at the same time at one shot, which can facilitate inventory management of the trial lens 18" manufactured from the lens portion 18A.

According to the present embodiment described above, the trial lens 18" is plastic and integrally formed with the grip portion 18B on the periphery of the lens portion 18, the grip portion 18B being gripped when the trial lens 18" is set in the trial frames 24. Since the grip portion 18B is molded simultaneously with the lens portion 18A, the process of manufacturing members for grip portions with different materials from lenses and attaching the members on lenses is omitted, which facilitates the whole trial lens manufacturing process.

The grip portion 18B is not metal, but formed of the same synthetic resin as the lens portion 18A, thus making the trial lens 18" more lightweight as a whole. Furthermore, the grip portion 18B is integrally molded with the lens portion 18A, which differs from the process when a grip portion is attached to a lens portion by means of caulking a holder ring provided with a grip portion on the periphery of the lens portion.

Consequently, the accurate position of the grip portion 18B laid out in relation to the lens position 18A is obtained, securing high optical precision of the lens portion 18A. Even when the holder ring 22 is attached on the periphery of the lens portion 18A, the holder ring 22 does not need to be strongly caulked on the lens portion 18A, thereby preserving high optical precision of the lens portion 18A.

The plastic trial lens 18" according to the present embodiment can be manufactured by means of the injection molding method or the injection compression molding method. Even if the molten synthetic resin for the material shrinks when cooling and solidifying by a high-pressure injection force or compression force applied at the time of molding, the mold transfer precision is sufficient to attain the high precision required for the trial lens. Moreover, one cycle of the molding process by the injection molding method or the injection compression molding method is extremely shorter than that by a conventional casting method, which makes the mass-production of the trial lenses possible and increases the manufacturing efficiency.

In addition, the injection molded product 18' for making the above-described trial lens 18" is provided with the liquid guiding and collecting area 18C. When the injection molded product 18' is dipped into and pulled up from the hard coating liquid 21, the hard coating liquid flowing down and dripping on the surfaces of the lens portion 18A can be guided to the liquid guiding and collecting area 18C. At the same time, a small amount of the remaining liquid without dripping down forms a liquid collected portion in the liquid guiding and collecting area 18C, which assures the uniformity of the thickness of the coating film covering the surfaces of the lens portion 18A without being affected by the liquid collected portion.

Since the liquid guiding and collecting area 18C, as well as the grip portion 18B, is integrally molded on the periphery of the lens portion 18A, the liquid guiding and collecting area 18C is molded simultaneously with the lens portion 18A.

The liquid guiding and collecting area 18C is shaped into a bar extending in an outside diametrical direction of the lens portion 18A. Consequently, the liquid collected portion formed with the remaining liquid without dripping is isolated from the lens portion 18A, thus surely making the thickness of the coating film formed on the lens portion 18A more uniform. In addition, the trial lens 18" is completed by removing the liquid guiding and collecting area 18C from the injection molded product 18'. The liquid guiding and collecting area 18C is shaped into a bar with a small connecting area with the lens portion 18A, which facilitates the removing process.

The grip portion 18B and the liquid guiding and collecting area 18C are formed opposite to each other on the periphery of the lens portion 18A. The injection molded product 18' is dipped into and pulled up from the hard coating liquid 21 placing the liquid guiding and collecting area 18C downward by supporting the grip portion 18B that projects upward with the supporting utensil 20. Therefore, the grip portion 18B is used both as a grip when the trial lens 18" is set in the trial frames 24 and as a support when the injection molded product 18' is dipped into the hard coating liquid 21.

Figure 5:
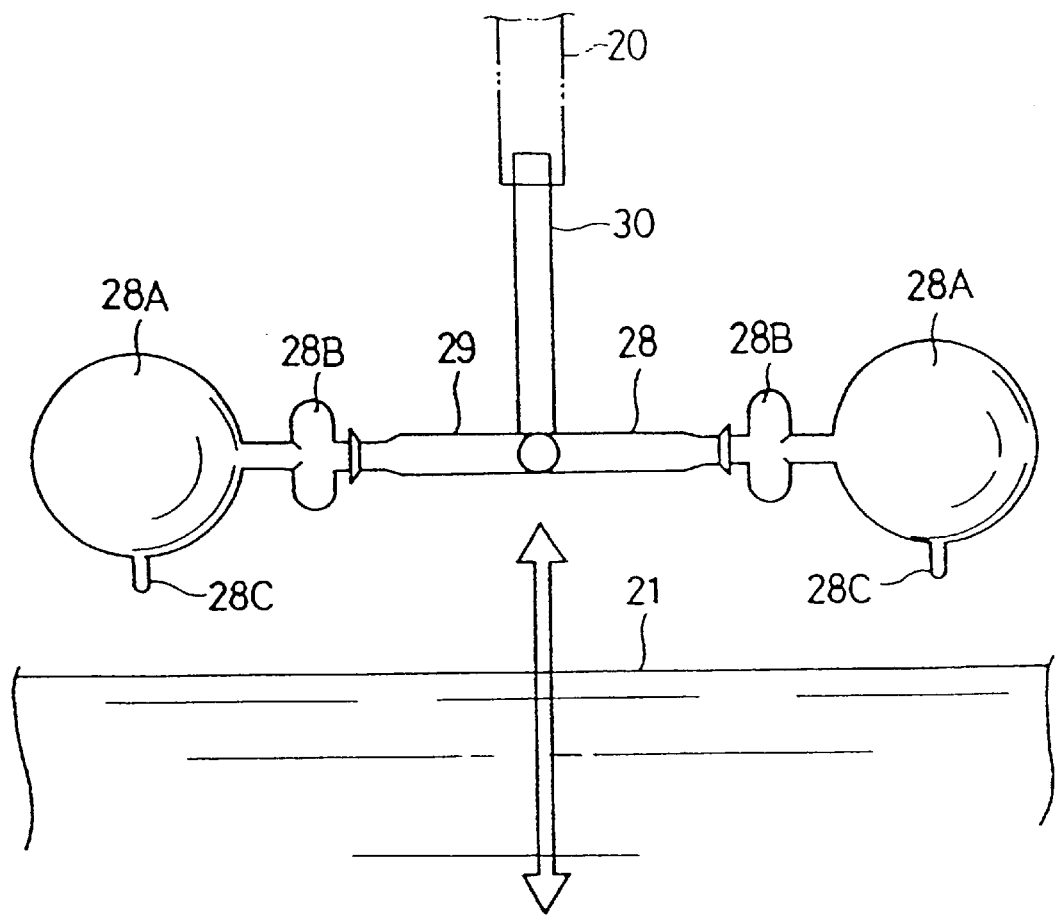
FIG. 5 is an explanatory view showing the process of coating an injection molded product in which more than one lens portions are coupled with a coupling portion.

FIG. 5 schematically illustrates an injection molded product 28 according to another embodiment of the present invention. The injection molded product 28 is provided with two pieces of a lens portion 28A. These two lens portions 28A are coupled through a grip portion 28B by means of a coupling portion 29. The coupling portion 29 is formed of a synthetic resin filled into a runner in the mold assembly of the injection compression molding machine. A supported portion 30 extends from the coupling portion 29, the supported portion being placed upward when the injection molded product 28 is dipped into the hard coating liquid 21. The supported portion 30 is formed by filling synthetic resin in a hollow space adjacent to the runner in the mold assembly.

Each of the lens portions 28A is provided with a bar-shaped liquid guiding and collecting area 28C on an opposite side to the supported portion 30 on the periphery of the lens portion.

When the injection molded product 28 is dipped into the hard coating liquid 21, the supported portion 30 projecting upward is supported with the supporting utensil 20. As a result, two pieces of the lens portions 28A are dipped into the hard coating liquid 21 at the same time. Moreover, since all the liquid collecting and guiding areas 28C are disposed downward when pulled up, the hard coat liquid flowing down on the surfaces of each lens portion 28A is guided to the liquid guiding and collecting area 28C for dripping down and a small amount of the remaining liquid without dripping down forms a liquid collected portion in the liquid guiding and collecting area 28C in the same way as the above-described embodiment.

Figure 6:
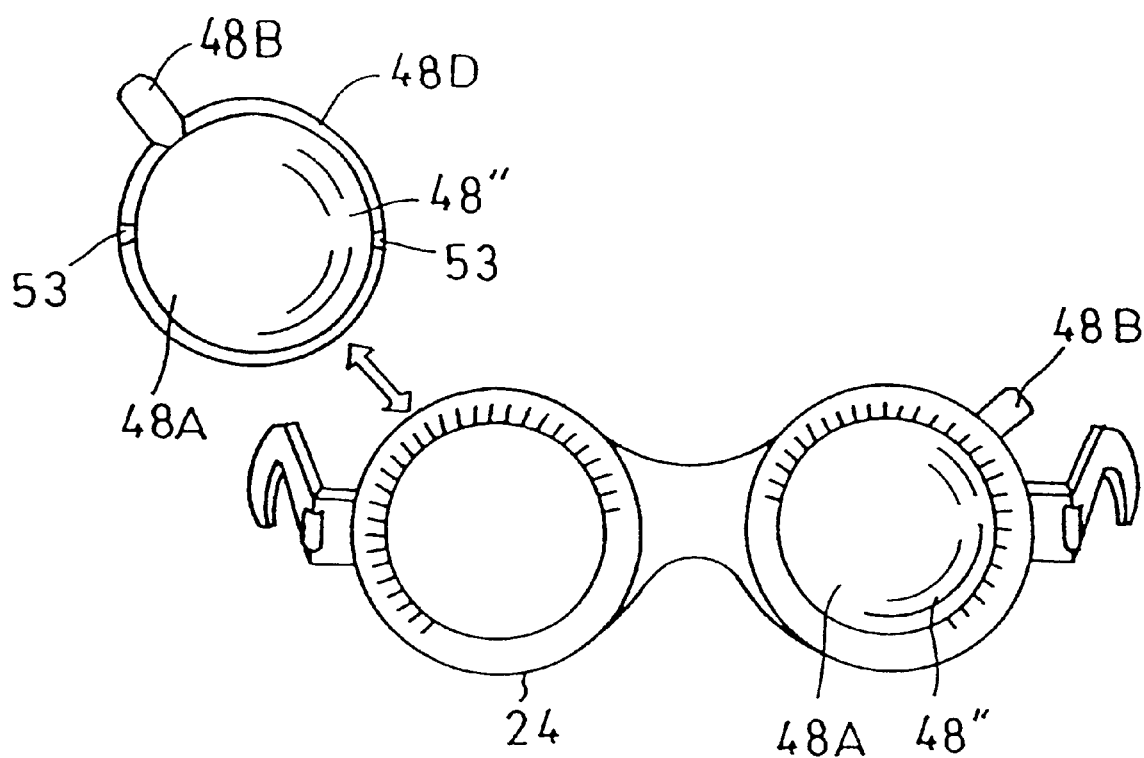
FIG. 6 is an explanatory view showing the process of setting a trial lens in trial frames for trial lenses according to an embodiment in which a grip portion serves as a liquid guiding and collecting area.

FIG. 6 shows a trial lens 48" according to still another embodiment. The trial lens 48" is formed from a secondary injection molded product 48' in FIG. 7 obtained from a primary injection molded product 48 in FIG. 9. The secondary injection molded product 48' is provided with a lens portion 48A, a grip portion 48B molded on a periphery of the lens portion 48A simultaneously with the lens portion 48A and a bar-shaped supported portion 48C formed on the opposite side to the grip portion 48B on the periphery of the lens portion 48A. The supported portion 48C is a portion supported with the supporting utensil when the injection molded product 48' is treated with a coating, and molded simultaneously with the lens portion 48A and the grip portion 48B. Consequently, the process of molding the injection molded product 48' including the supported portion 48C is simplified.

Figure 7:
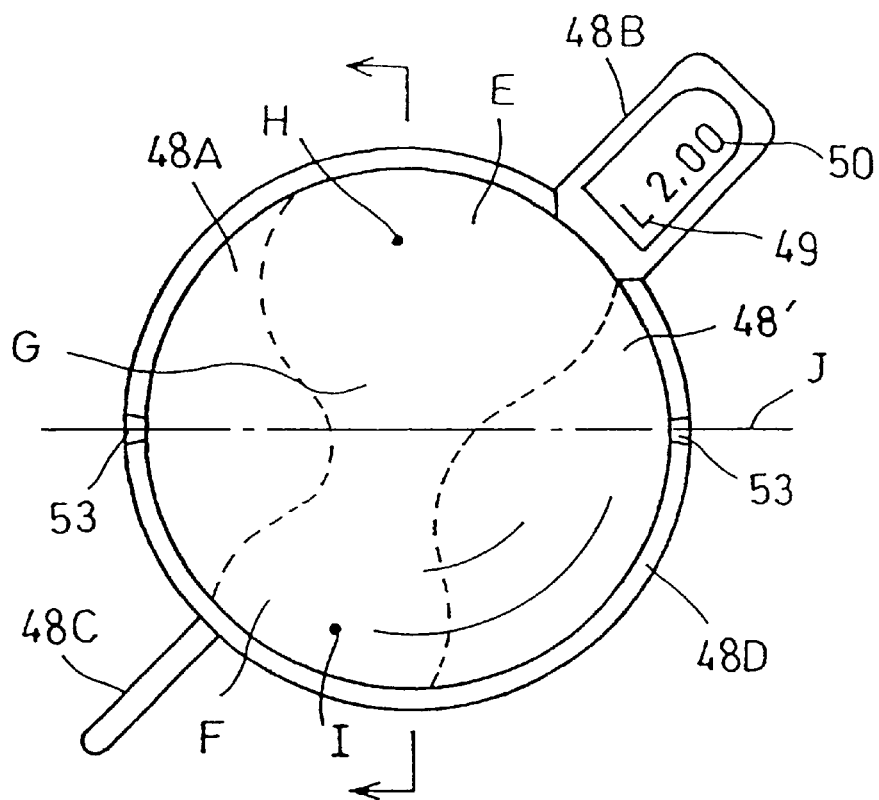
FIG. 7 is a schematic view of an injection molded product to obtain the trial lens in FIG. 6.

The lens portion 48A is a progressive multifocal lens portion having a portion for far vision E, a portion for near vision F, and a progressive portion G between the portion for far vision E and the portion for near vision F. In FIG. 7, an eye point of the portion for far vision E is represented by H and an eye point of the portion of near vision F is represented by I, respectively.

The grip portion 48B is provided with an indication 49 for distinguishing between the right and the left which shows the lens portion 48A in the injection molded product 48' is for a right eye or a left eye, and an addition indication 50 which shows the addition of the lens portion 48A in the injection molded product 48'. The indications 49 and 50 are formed with a mark engraved on a member composing the mold assembly in the injection compression molding machine when the grip portion 48B is molded simultaneously with the lens portion 48A.

Figure 8:
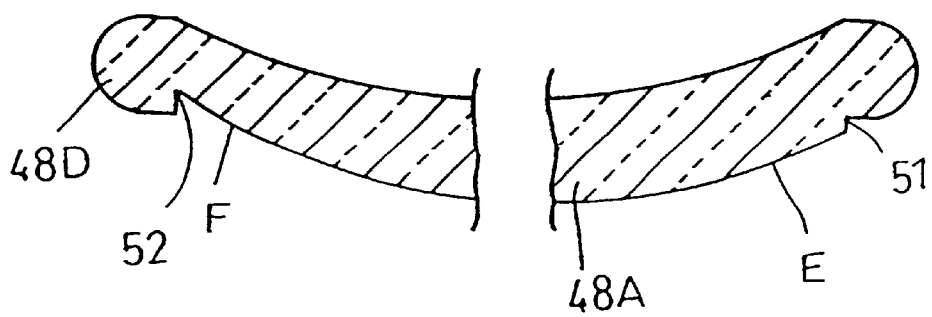
FIG. 8 is a sectional view taken along the B-B line in FIG. 7.

As shown in FIG. 8, integrally molded with the lens portion 48A on the periphery of the lens portion 48A is an edge portion 48D which, as well as the grip portion 48B and the supported portion 48C, is molded simultaneously with the lens portion 48A. The edge portion 48D is divided from the portions for far vision E and near vision F in the lens portion 48A respectively by a step 51 and a groove 52. The edge portion 48D which is thicker than the portion for near vision F is substituted for the holder ring 22 shown in FIG. 4.

Consequently, the trial lens 48" shown in FIG. 6 according to the embodiment becomes more lightweight than the trial lens 18" in FIG. 4 in which the holder ring 22 is attached on the periphery of the lens portion 18A.

The grip portion 48B shown in FIG. 7 is formed shifting to the right or the left at an angle of 45 degrees from the center between the right portion and the left portion of the lens portion 48A according to whether the lens portion 48A in the injection molded product 48' is manufactured for a right eye or a left eye. That is, when the trial lens 48" obtained from the injection molded product 48' is manufactured for a left eye, the grip portion 48B is formed at an angle of 45 degrees to the left of the lens portion 48A as seen from a testee who wears trial frames 24 in FIG. 6, and when the trial lens 48" is manufactured for a right eye, the grip portion 48A is formed at an angle of 45 degrees to the right of the lens portion 48A as seen from a testee. The lens portion 48A of the injection molded product 48' in FIG. 7 is manufactured for a left eye.

In the edge portion 48D on the periphery of the lens portion 48A, marks 53 showing the direction of a horizontal datum line J are formed in points located on both sides of the lens portion 48A when the lens portion 48A is disposed in a correct vertical direction as FIG. 7 shows. The marks 53 are portions indented in some points of the edge portion 48D and molded by means of projected portions formed in a component member of the mold assembly simultaneously with the lens portion 48A, the grip portion 48B, the supported portion 48C, and the edge portion 48D.

The marks 53 show the horizontal direction of the lens portion 48A and the grip portion 48B shows the lens portion 48A is for a right eye or a left eye so that the trial lenses 48" for a right eye and a left eye can be distinguished while a position of the revolving direction of the circular lens portion 48A of each trial lens 48" is accurately fixed when the trial lens 48" obtained from the injection molded product 48' is set in the trial frames 24 in FIG. 6. Consequently, the trial lenses 48" can be correctly set in the trial frames 24. In addition, a diopter measuring position in the portions for far vision E and near vision F in the lens portion 48A or layout of optical center can be easily known.

The above-described trial lens 48" shown in FIG. 6 is 38 millimeters in the whole diameter including the edge portion 48D, the edge portion 48 is 1.5 millimeters in width, the lens portion 48A is 35 millimeters in diameter, and the grip portion 48B is 15 millimeters in length and 9 millimeters in width.

Figure 9:
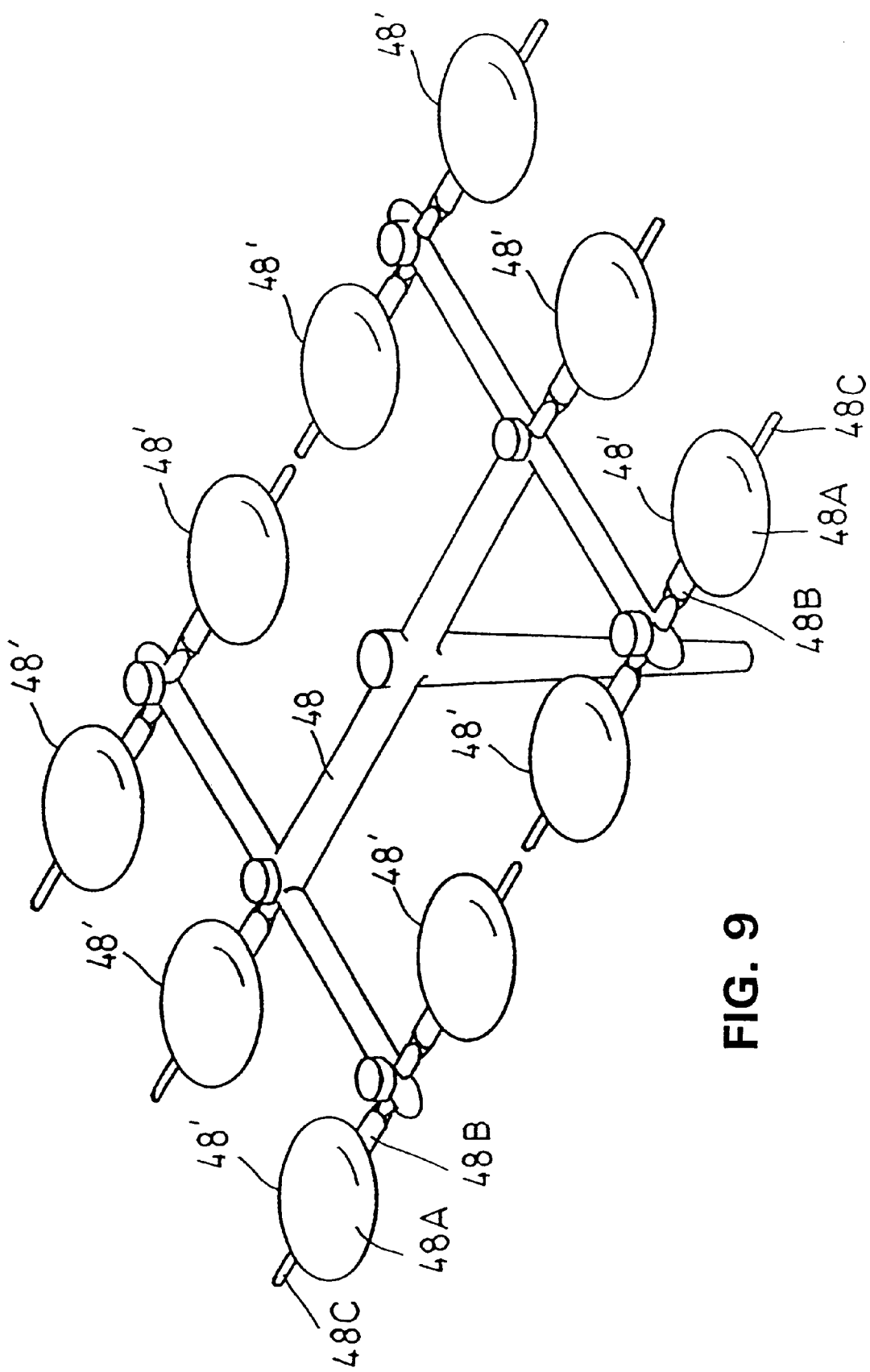
FIG. 9 is a perspective view showing a whole injection molded product in which more than one injection molded product in FIG. 7 are formed.

The primary injection molded product 48 shown in FIG. 9 is manufactured to obtain a total of ten secondary injection molded products 48' for progressive multifocal lenses arranged connectingly to each other two-dimensionally. The progressive multifocal lenses have five kinds of additions ranging from 1.00 diopter to 3.00 diopter at an interval of 0.5 diopter pitch. Every two injection molded products 48' have the lens portions 48A with the same addition.

Figure 10:
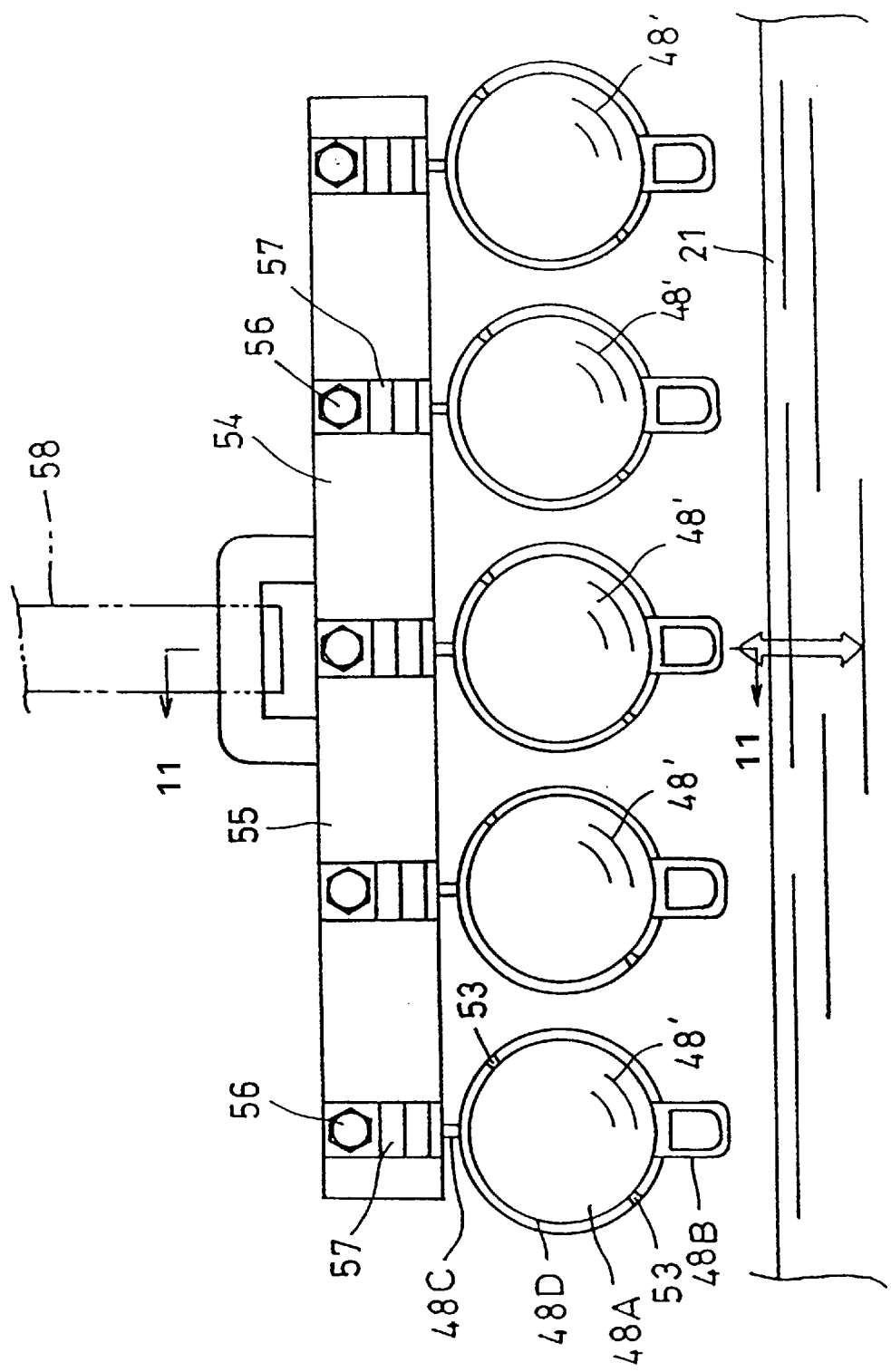
FIG. 10 is an explanatory view showing the process of coating more than one injection molded product in FIG. 7 obtained from the injection molded product in FIG. 9.
Figure 11:
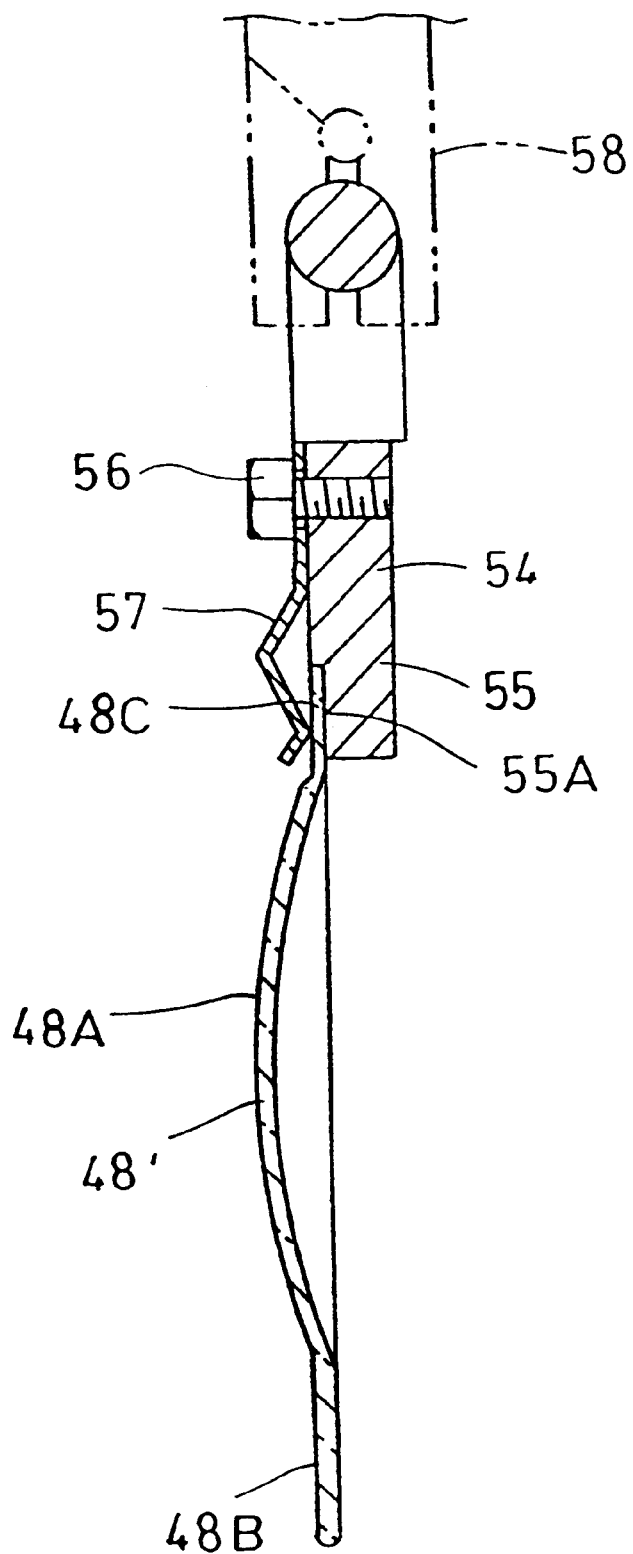
FIG. 11 is a sectional view taken along the C—C line in FIG. 10.

Each secondary injection molded product 48' is obtained by being cut from the primary injection molded product 48 at a forward end of the grip portion 48B. Thereafter, a total of five secondary injection molded products 48' are hung supportively with a supporting utensil 54 shown in FIGS. 10 and 11 for coating. The supporting utensil 54 includes a body 55 with five slots 55A formed upward from a lower surface into which bar-shaped supported portions 48C of the injection molded products 48' can be inserted, and clipping members 57 composed of flat springs of which the upper portions are fastened to the body 55 with screws 56, the clipping members being provided on every slot 55A. After the screws 56 are loosened, the supported portions 48C of the injection molded products 48' are inserted into each slot 55A, the screws 56 are tightened, and hence each injection molded product 48' is hung supportively by the supported portion 48C being clipped with the body 55 and the clipping member 57.

The supporting portion 54 is gripped with a gripping utensil 58. In this situation, the injection molded products 48' are dipped into and pulled up from the hard coating liquid 21 that is the coating liquid. The dipping process is conducted by placing the supported portions 48C upward and the grip portions 48C downward. In this embodiment, a surplus of hard coating liquid flowing down on surfaces of the lens portion 48A is guided to the grip portion 48B for dripping down and the remaining hard coating liquid without dripping down forms a liquid collected portion in the grip portion 48B, that is, in this embodiment the grip portion 48B also serves as a liquid guiding and collecting area.

The injected molded product is treated dipping as described above and then heat-dried, thereby making a coating film with the hard coating liquid on the surfaces of the lens portion 48A. Afterward, the supported position 48 is removed by cutting and a label mentioning the same information as the foregoing indications 49 and 50 shown in the grip portion 48B is stuck to the grip portion 48B, thereby finishing the trial lens 48" in FIG. 6.

When the supported portion 48C is removed by cutting, the supported portion 48 is shaped into a bar extending in an outside diametrical direction of the lens portion 48A with a small connecting area with the edge portion 48D on the periphery of the lens portion 48A, which facilitates the cutting process.

The grip portion 48B which also serves as the liquid guiding and collecting area is formed on the periphery of the lens portion 48A on the side of the portion for far vision E out of the sides of portions for far vision E and near vision F in the lens portion 48A. If the grip portion 48B is formed on the periphery of the lens portion 48 on the side of the portion for near vision F, since the groove 52 is formed depending a sectional shape of the portion for near vision F between the portion for near vision F and the edge portion 48C as shown in FIG. 8, the hard coating liquid is collected in the groove 52 when the injection molded product is pulled up from the hard coating liquid, which affects the optical precision of the lens portion 48A. However, this embodiment can prevent the disadvantage described above the breaking out.

Figure 12:
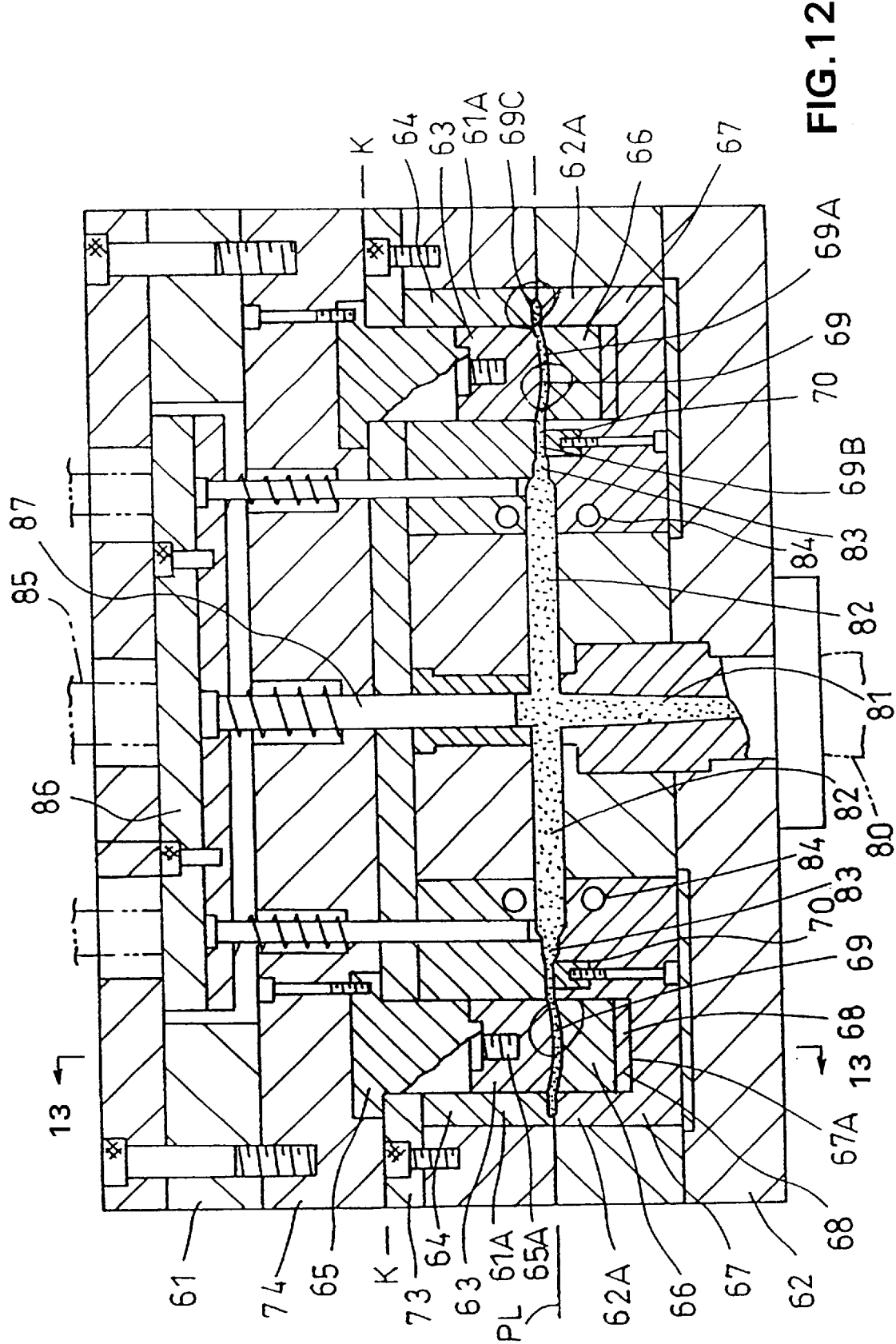
FIG. 12 is a vertical sectional view of a mold assembly for injection compression molding to manufacture the injection molded product in FIG. 9.
Figure 13:
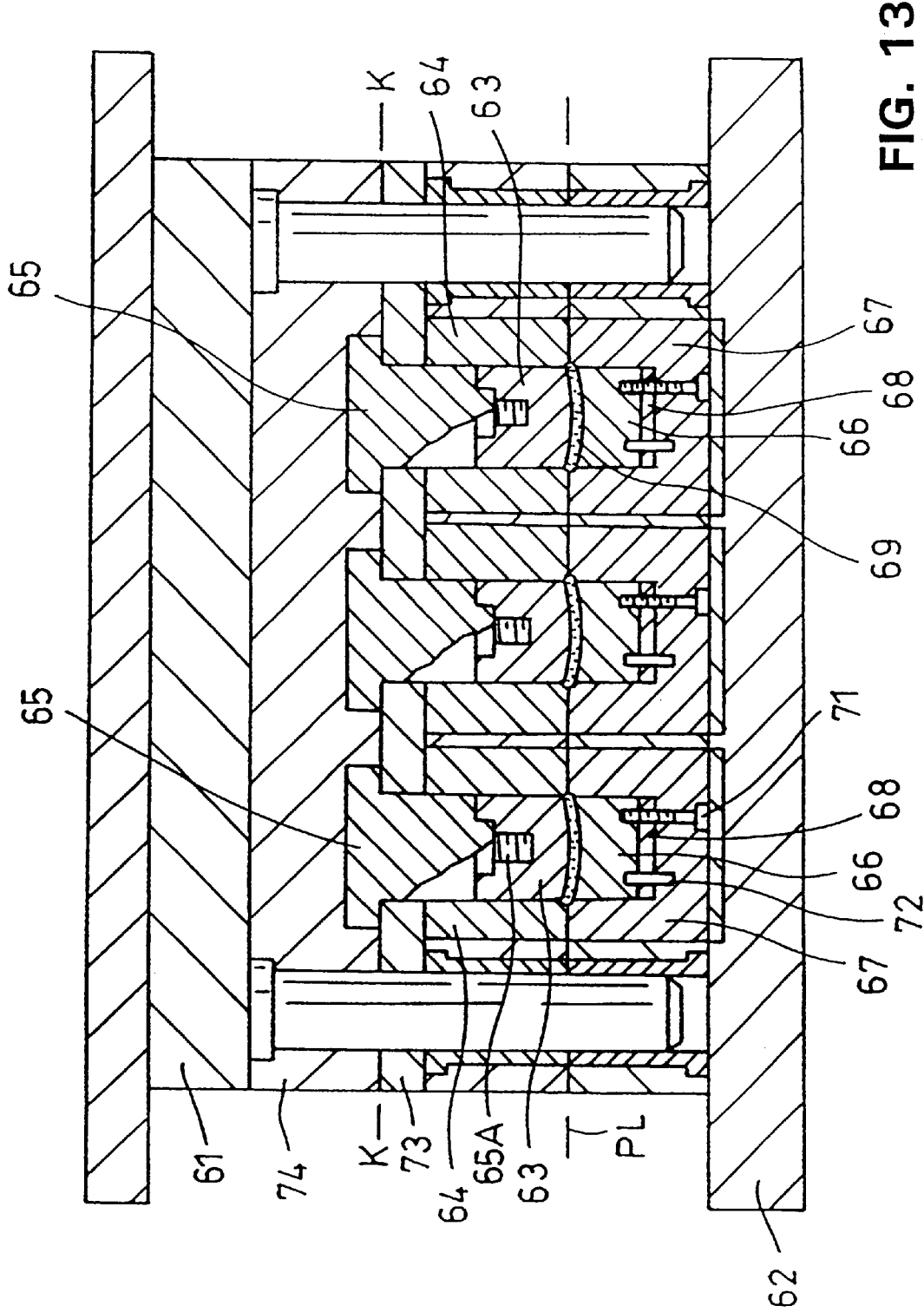
FIG. 13 is a sectional view taken along the D—D line in FIG. 12.

FIGS. 12 and 13 show a mold assembly in an injection compression molding machine for molding the primary injection molded product 48 in FIG. 9. The mold assembly is provided with a top mold 61 and a bottom mold 62, both of which a parting line PL divides. The top mold 61 contains an inner insert member 63, an outer insert member 64 disposed on the outside of the inner insert member 63, and a back insert 65 disposed on the back side of the inner insert member 63, in other words, on the upper side of the inner insert member 63. The bottom mold 62 contains an inner insert member 66, an outer insert member 67 disposed on the outside of the inner insert member 66 which is built in a hollow portion 67A, and a spacer 68 for adjusting the thickness of a lens disposed on the back side of the inner insert member 66, in other words, on the lower side of the inner insert member 66, and between the inner insert member 66 and the outer insert member 67.

The inner insert member 63 in the top mold 61 and the inner insert member 66 in the bottom mold 62 are vertically disposed opposite to each other. The outer insert member 64 in the top mold 61 and the outer insert member 67 in the bottom mold 62 are also vertically disposed opposite to each other. An insert 61A in the top mold 61 is formed with the inner and the outer insert members 63 and 64 in the top mold 61, and a corresponding insert 62A in the bottom mold 62 is formed with the inner and the outer insert members 66 and 67 in the bottom mold 62. The number of a pair of the inserts 61A and 62A disposed vertically is the same as the number of sets of the secondary injection molded products 48' manufactured from the primary injection molded product 48 shown in FIG. 9. When the top mold 61 and the bottom mold 62 are mold-closed, a cavity 69 is formed between a pair of inserts 61A and 62A disposed vertically in each set, the cavity 69 containing a lens molded portion 69A, a grip molded portion 69B, and a supported portion molded portion 69C.

The lens molded portion 69A is formed between the inner insert members 63 and 66 in the top and the bottom molds 61 and 62, respectively. The grip molded portion 69B and the supported portion molded portion 69C are formed between the outer insert members 64 and 67 in the top and the bottom molds 61 and 62, respectively. An engraving mark member 70 is disposed on a spot corresponding to the grip molded portion 69B in the outer insert member 67 in the bottom mold 62. When the lens portion 48A, the grip portion 48B and the supported portion 48C in FIG. 7 are molded by filling molten synthetic resin in a cavity 69, the indications 49 and 50 are provided on the grip portion 48B by means of the engraving mark member 70.

Figure 15:
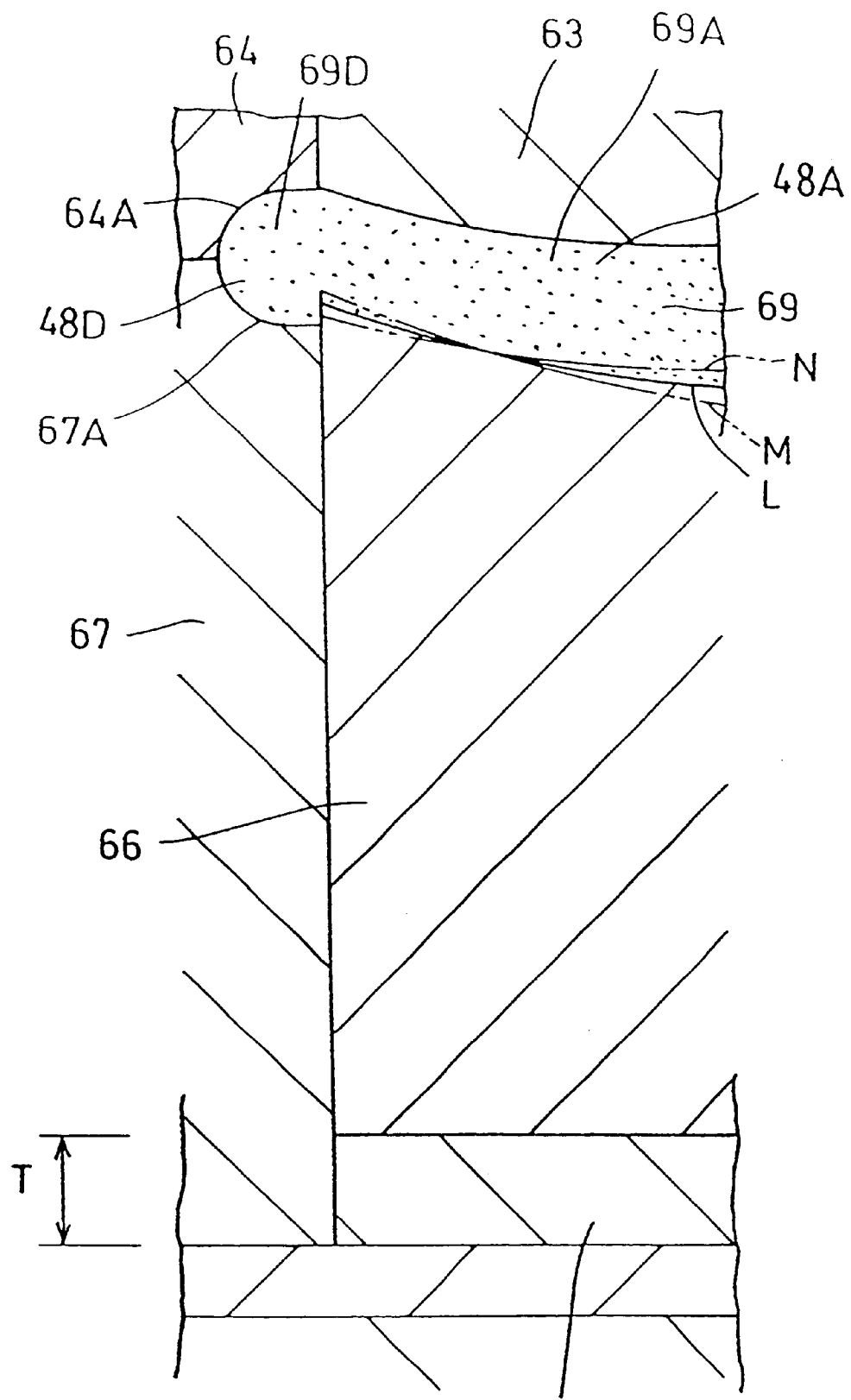
FIG. 15 is a schematic view showing a spacer and the surroundings in case of molding more than one kind of progressive multifocal lens with different additions by means of the spacer for adjusting a thickness disposed on the back side of one insert out of a pair of the inserts.

As shown in FIG. 15, recessed portions 64A and 67A are formed in the outer inserts members 64 and 67 in the top and the bottom molds 61 and 62, respectively. When the molten synthetic resin is filled in the cavity 69, the edge portion 48D serving as the holder ring is formed on the periphery of the lens portion 48A as shown in FIGS. 7 and 8. Therefore, a space between the recessed portions 64A and 67A is an edge molded portion 69D in the cavity 69. Moreover, provided in the outer insert member 67 in the bottom mold 62 is a projection to form the mark 53 with the dented portion shown in FIG. 7 on the edge portion 48D.

As shown in FIG. 12, the back insert 65 is integrally provided with a male screw portion 65A extending downward. The back insert 65 and the inner insert member 63 are joined together by the male screw portion 65A being tightened into a hole of a female screw. As shown in FIG. 13, the inner insert member 66 in the bottom mold 62 is joined to the outer insert member 67 with a bolt 71.

The lens portion 48A molded in the lens molded portion 69A in the cavity 69 is a meniscus lens of which one surface is a concave surface from a spherical surface and the other surface is a convex surface from an aspherical surface. The concave surfaces of the lens portions 48A formed with the inner insert members 63 in the top mold 61 have the same curved surface in the progressive multifocal lenses with different additions. However, the convex surfaces of the lens portions 48A formed with the inner insert members 66 in the bottom mold 62 are required to have different curved surfaces in the progressive multifocal lenses with different additions. Therefore in the mold assembly according to the embodiment, five kinds of the inner insert members 66 are used to mold five kinds of progressive multifocal lenses as described above. The inner insert members 66 are positioned in the outer inserts 67 with a positioning pin 72 in FIG. 13 so that the inner insert members 66 are accurately located in the outer insert members 67 in a direction of rotation on a vertical axis.

The top mold 61 is vertically separated by a boundary section K—K between a mold plate 73 and a mold plate 74. When the top mold 61 and the bottom mold 62 are mold-closed, in relation to a portion below the mold plate 73 a portion above the mold plate 74 can vertically move in correspondence to a margin for compressing with a clamping cylinder and another cylinder. The back insert 65 and the inner insert member 63 in the top mold 61 are members joined to the mold plate 74 as shown clearly in FIG. 12 so that the back insert 65 and the inner insert member 63 vertically move with the mold plate 74.

When the top mold 61 and the bottom mold 62 are mold-closed, the molten synthetic resin is injected from an injection nozzle 80 shown in FIG. 12 in the injection compression molding machine. Subsequently, the molten synthetic resin is filled in each cavity 69 through a sprue 81, a runner 82, and a gate 83 inside the mold assembly. At this time, the back insert 65 and the inner insert member 63 rise in correspondence to the margin for compressing. After the molten synthetic resin is filled in the cavity 69, the back insert 65 and the inner insert member 63 descend. Thus is compressed the molten synthetic resin which is gradually cooled and solidified by a temperature controlling fluid passing through fluid flowing passages 84 in the top mold 61 and the bottom mold 62.

After the injection molded product 48 in FIG. 9 is molded by solidification of the molten synthetic resin, the top mold 61 and the bottom mold 62 are mold-opened from a paring line PL and the injection molded product 48 attached to the side of the top mold 61 is pushed out by means of a pin 87 in an ejecting plate 86 which is pushed down with a bar 85 in an ejecting cylinder.

The primary injection molded product 48 taken out from the mold assembly as described above is provided with ten secondary injection molded products 48'. Each secondary injection molded product 48' is provided with the lens portion 48A, the grip portion 48B, the supported portion 48C and the edge portion 48D. The grip portion 48B, the supported portion 48C and the edge portion 48D are molded simultaneously with the lens portion 48A. The indications 49 and 50 in FIG. 7 are provided in the grip portion 48B and the mark 53 is formed in the edge portion 48D.

As shown in FIG. 12, the grip molded portion 69B for molding the grip portion 48B in the cavity 69 is formed between the gate 83 from which the molten synthetic resin flows into the cavity 69 and the lens molded portion 69A in the cavity 69. Accordingly, when the molten synthetic resin flows into the cavity 69 from the gate 83, the molten synthetic resin is filled in the lens molded portion 69A through the grip molded portion 69B so that distortion in the filling of the molten synthetic resin is easy to break out in a portion of the resin near the gate 83, but no distortion occurs in a portion of the resin filled in the lens molded portion 69A, thus securing a high precision of the lens.

The inserts 61A and 62A making a pair which are disposed in the top mold 61 and the bottom mold 62 are composed of the inner insert member 63 and 66, and the outer insert members 64 and 67, respectively. The lens molded portion 69A is formed with the inner insert members 63 and 66, and the grip molded portion 69B and the like are formed with the outer inserts members 64 and 67. Consequently, when more than one type of trial lenses with different kinds, diopters, thicknesses and the like of the lens portions 48A provided with the grip portions 48B and the like integrally formed with the lens portions 48A on the periphery of the lens portions 48A are manufactured, only the inner insert members 63 and 66 need to be exchanged, while the outer insert members 64 and 67 are used in common for all sorts of trial lenses.

In this embodiment, the spacer 68 for adjusting the thickness is disposed on the back side of the inner insert member 66 in the bottom mold 62 as described above. A portion of the spacer 68 is shown in FIG. 15. The progressive multifocal lens portion 48A, which is molded in the lens molded portion 69A in the cavity 69, is provided with five kinds of additions ranging from 1.00 diopter to 3.00 diopter at intervals of 0.5 pitch as stated above. A solid line L shown in FIG. 15 is a convex curved line of the lens portion 48A with an addition of 2.00 diopter, two-dot chain line M is a convex curved line of the lens portion 48A with an addition of 3.00 diopter, and two-dot chain line N is a convex curved line of the lens portion 48A with an addition of 1.00 diopter.

The capacity of each cavity 69 to mold five kinds of the lens portions 48A, that is, the volume of the lens portion differs in specifications based on the usual design of lenses. However, as the difference in capacity among the cavities 69 becomes larger, the difference in the amount of filling of the molten synthetic resin is enlarged, which causes an unevenness in molding conditions, and furthermore makes it difficult to assure a high optical precision of the lens portions 48A to be molded.

Consequently, in the embodiment, the volume of the lens portion with an intermediate addition of 2.00 diopter is a standard in the stage of designing lenses. The thickness of other lens portions with other additions is modified to accord with the volume.

The aforesaid is explained from the side of the mold assembly hereinafter. The spacers 68 with the same five kinds of thicknesses as additions are used. A thickness T of the spacer 68 with the intermediate thickness is fixed as a thickness of the lens portion 48A with the intermediate addition of 2.00 diopter out of additions ranging from 1.00 diopter to 3.00 diopter. The thickness of a spacer of the lens portion 48A with an addition above 2.00 diopter and the thickness of a spacer of the lens portion 48A with an addition below 2.00 diopter are fixed on the basis of the thickness T. Each of spacers 68 with five kinds of thickness thus obtained is disposed on the back side of the inner insert member 66 to mold the lens portion 48A with each addition.

As a result, when five kinds of progressive multifocal lens portions 48A with different additions are manufactured at one shot by means of the mold assembly in the injection compression molding machine, the capacity of each cavity 69 can be averaged so that molding conditions of each lens portion 48A with each of the additions can be averaged, thus manufacturing each of the lens portions 48A with a high optical precision.

Figure 14:
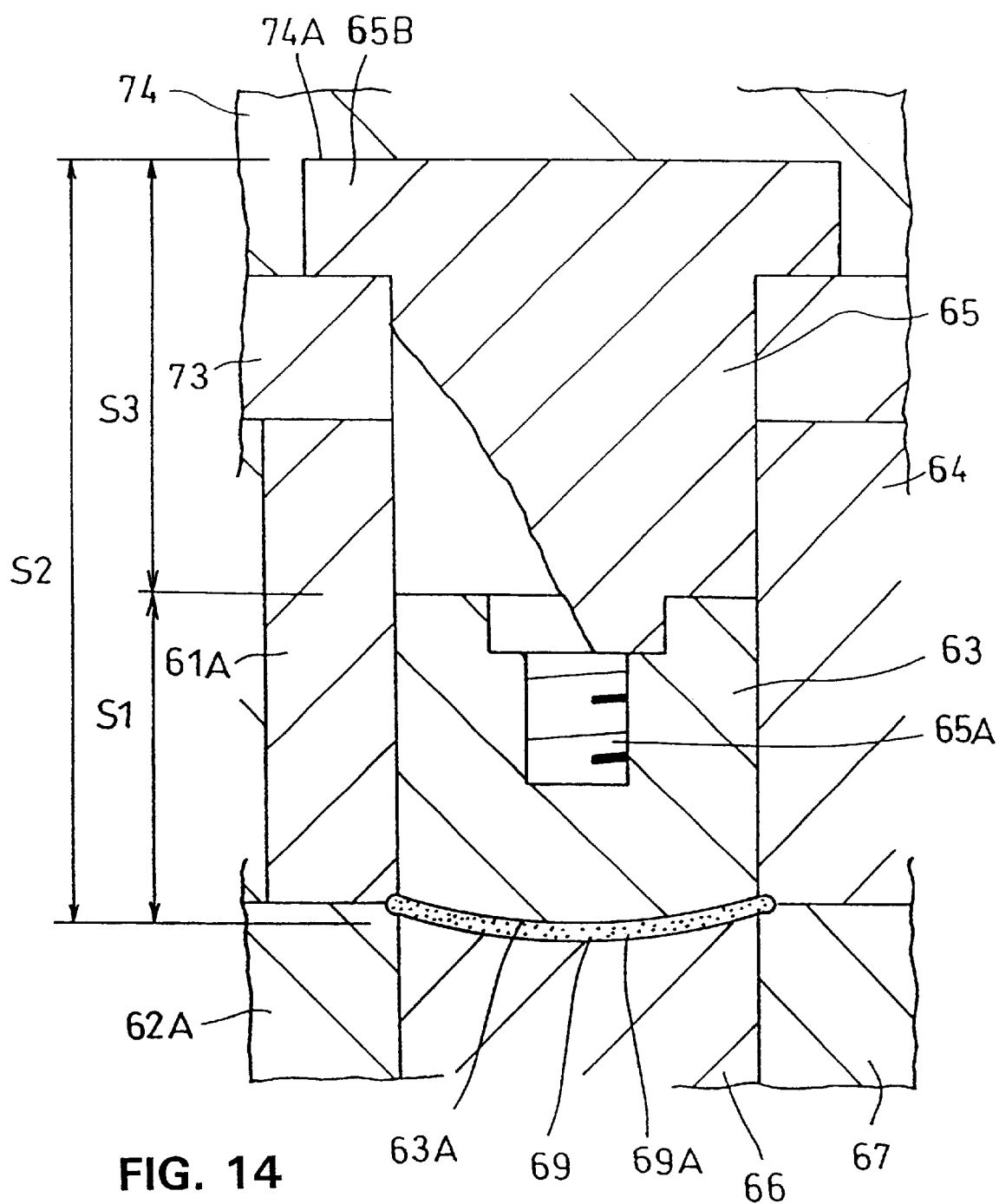
FIG. 14 is a fragmentary enlarged view of FIG. 13 showing a pair of inserts forming a cavity.

To obtain the lens portion 48A with a pre-determined thickness, the position of a lens molded surface in the inner insert member 63 in the top mold 61 in relation to the inner insert member 66 in the bottom mold 62 is located in the pre-determined vertical direction position, and hence, in the embodiment, the back insert 65 is disposed on the back side of the inner insert member 63 in the top mold 1 as shown in FIG. 14.

In the embodiment, a length S1 of the inner insert member 63 has an error compared with the original length and the initial length of the back insert 65 is a little larger than the original length. After the inner insert member 63 and the back insert 65 are joined with the male screw portion 65A, an upper surface of the back insert 65 is cut to obtain the accurate vertical direction position of the lens molded surface 63A of the inner insert member 63 in the top mold 61 in relation to the inner insert member 66 in the bottom mold 62 by means of a total length S2 of the inner insert member 63 and the back insert 65, then a length S3 of the back insert 65 is finished to obtain the total length S2.

Consequently, the accurate vertical directional position of the lens molded surface 63A is fixed by the length of the back insert 65, and therefore in the inner insert member 63 only the lens molded surface 63A needs to be high-precisely finished, which facilitates the work of manufacturing and processing the inner insert member 63.

When the length of the back insert 65 is S3, the thickness of a head portion 65B of the back insert 65 is the same as or a little larger than a depth of a recessed portion 73A in the mold plate 74. Thus, also when the back insert 65 is joined with the mold plate 74, the accurate vertical directional position of the lens molded surface 63A in the inner insert member 63 can be obtained, and in addition, detachment of the mold plates 73 and 74 to get the margin for compressing is possible.

Industrial Availability

As described above, a plastic trial lens, an injection molded product for making the trial lens and a mold assembly for molding the injection molded product according to the present invention are useful since a grip portion is integrally formed on a periphery of a lens portion, the grip portion being gripped when the plastic trial lens is set in trial frames for trial lenses.

What is claimed is:

1. An injection molded product for making plastic trial lenses comprising:

a lens portion;

a liquid guiding and collecting area integrally formed on a periphery of said lens portion, in which coating liquid flowing down on surfaces of the lens portion is guided and collected when dipped into and pulled up from the coating liquid; and a grip portion gripped when said lens portion is set in the trial frames after said liquid guiding and collecting area is removed, said liquid guided and collecting area and said grip portion being molded simultaneously with said lens portion.

2. The injection molded product for making the plastic trial lenses according to claim 1, wherein said liquid guiding and collecting area is shaped into a bar extending in an outside diametrical direction of said lens portion.

3. The injection molded product for making the plastic trial lenses according to claims 1, wherein said liquid guiding and collecting area and said grip portion are formed opposite to each other on the periphery of said lens portion.

4. The injection molded product for making the plastic trial lenses according to claim 1, wherein a plurality of said lens portions are coupled with each other by means of a coupling portion, the coupling portion being provided with a supported portion supported with a supporting utensil when said lens portions are dipped into the coating liquid, and said liquid guiding and collecting area is formed on an opposite side to the supported portion on the periphery of each of said lens portions.

5. An injection molded product for making plastic trial lenses comprising:

a lens portion; and a grip portion molded on a periphery of said lens portion simultaneously with the lens portion being gripped when said lens portion is set in trial frames for trial lenses, the grip portion being disposed downward when said lens portion is dipped into coating liquid, thereby serving also as a liquid guiding and collecting area to guide and collect the coating liquid flowing down on surfaces of said lens portion when said lens portion is pulled up from the coating liquid.

6. The injection molded product for making the plastic trial lenses according to claim 5, wherein said lens portion is a progressive multifocal lens portion with a portion for far vision, a portion for near vision, and a progressive portion between the portion for far vision and the portion for near vision, and said grip portion is formed on a periphery of said lens portion on the side of the portion for far vision out of the portion for far vision and the portion for near vision.

7. The injection molded product for making the plastic trial lenses according to claim 5, wherein a supported portion is provided on the opposite side to said grip portion on the periphery of said lens portion, the supported portion being supported with a supporting utensil when said lens portion is dipped into the coating liquid.

8. The injection molded product for making the plastic trial lenses according to claim 5, wherein the supported portion is molded simultaneously with said lens portion and said grip portion.

9. The injection molded product for making the plastic trial lenses according to claim 8, wherein the supported portion is shaped into a bar extending in an outside diametrical direction of said lens portion.

10. A plastic trial lens comprising: a lens portion; a grip portion formed on a periphery of the lens portion; an edge portion provided integrally on the periphery of the lens portion; and a mark provided on said edge portion for indicating a direction of a horizontal datum line, wherein said lens portion is a progressive multifocal lens portion having a far vision portion, a near vision portion and a progressive portion provided between the far vision portion and the near vision portion, said grip portion being provided on the right or left periphery of the lens portion depending on whether the lens is for the right eye or a left eye and said lens portion, grip portion, edge portion and mark are molded simultaneously when they are molded by an injection compression molding method.

11. The plastic trial lens of claim 10, wherein said lens portion has a convex surface which is a meniscus lens having an aspheric progressive surface and a spherical concave surface.

12. The plastic trial lens of claim 11, wherein the curvature of the concave surface is fixed.

13. A plastic trial lens comprising: a lens portion; a grip portion formed integrally on the periphery of the lens portion for being gripped when the lens portion is set in glass frames; an edge portion provided integrally on the periphery of the lens portion in place of a holder ring; and a mark provided in the form of an indented portion provided in the edge portion for indicating a horizontal datum line, wherein said lens portion is a progressive multifocal lens portion having a far vision portion, a near vision portion and a progressive portion provided between the far vision portion and the near vision portion, said grip portion is provided on the right or left periphery of the lens portion depending on whether the lens is for a right eye or a left eye and said lens portion, grip portion, edge portion and mark are molded simultaneously when they are molded by an injection compression molding method.

14. The plastic trial lens of claim 13, wherein said lens portion has a convex surface which is a meniscus lens having an aspheric progressive surface and a spherical concave surface.

15. The plastic trial lens of claim 14, wherein the curvature of the concave surface is fixed.

* * * * *